United States Patent [19]

Chabala et al.

[11] Patent Number: 4,751,237

[45] Date of Patent: Jun. 14, 1988

[54] ANTIHYPERCHOLESTEROLEMIC BETA-LACTONES

[75] Inventors: John C. Chabala; Arthur A. Patchett, both of Westfield, N.J.; Michael D. Greenspan, New York, N.Y.

[73] Assignee: Merck & Co., Inc., Rahway, N.J.

[21] Appl. No.: 856,316

[22] Filed: Apr. 28, 1986

Related U.S. Application Data

[63] Continuation-in-part of Ser. No. 822,501, Jan. 27, 1986, abandoned.

[51] Int. Cl.$^4$ .................... A61K 31/335; A61K 31/74

[52] U.S. Cl. ....................................... 514/449; 424/78

[58] Field of Search ............... 549/263, 279, 283, 328, 549/329; 436/71; 514/449; 424/78

[56] References Cited

U.S. PATENT DOCUMENTS

| | | | |
|---|---|---|---|
| 2,970,053 | 1/1961 | Martin et al. | 424/79 |
| 3,074,795 | 1/1963 | Friedman et al. | 424/79 |
| 3,538,216 | 11/1970 | Polin | 424/79 |

OTHER PUBLICATIONS

Chemical Communications, 1970, p. 639 [(Chem. Abstracts; vol. 73 #55594j (1970)].

J. Chem. Soc. (c), 1971, pp. 3888-3890 [(Chem. Abstracts; vol. 76, #45686p (1972)].

*Primary Examiner*—Allen J. Robinson

*Assistant Examiner*—Richard Kearse

*Attorney, Agent, or Firm*—Joseph F. DiPrima; Michael C. Sudol

[57] ABSTRACT

The compounds of the following general structural formula (I)

(I)

HO … $CO_2R$ … O … O wherein R is hydrogen or $C_{1-3}$alkyl and the tetrahydro analogs thereof, are 3-hydroxy-3-methylglutarylcoenzyme A (HMG-CoA) synthase inhibitors and useful as antihypercholesterolemic agents for the treatment of disease in which the inhibition of cholesterol biosynthesis would by useful, such as arteriosclerosis, hyperlipidemia and familial hypercholesterolemia.

8 Claims, No Drawings

ANTIHYPERCHOLESTEROLEMIC BETA-LACTONES

This is a continuation-in-part of U.S. patent application Ser. No. 822,501, filed Jan. 27, 1986, now abandoned.

BACKGROUND OF THE INVENTION

The compound of the formula (I), wherein R is hydrogen, 12-hydroxy-13-hydroxymethyl-3,5,7-trimethyltetradeca-2,4-dien-1,14 dioic acid 12,14-lactone, was identified as an antibiotic fungal metabolite in 1970 [Aldridge et al., *Chem. Comm.*, 1970, p. 639]. The compounds of the formula (I), wherein R is methyl and the tetrahydro analog wherein R is hydrogen were disclosed in the structure elucidation of the compound of the formula (I) wherein R is hydrogen [Alridge et al. *J. Chem. Soc.* (C), 1971, pp. 3888–3891].

SUMMARY OF THE INVENTION

This invention relates to the novel pharmacological properties of the compounds of the formula (I) which have been found to be HMG-CoA synthase inhibitors and are useful as antihypercholesterolemic agents either as the sole therapeutic agent or in combination with bile acid sequestrants.

DETAILED DESCRIPTION OF THE INVENTION

The present invention is directed to a method of inhibiting cholesterol biosynthesis which comprises the administration to a subject in need of such treatment a nontoxic therapeutically effective amount of a compound represented by the following general structural formula (I)

(I)

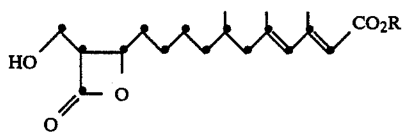

wherein R is hydrogen or $C_{1-3}$alkyl; the tetrahydroanalogs thereof; and pharmaceutically acceptable salts thereof.

The present invention is also directed to a method of inhibiting the activity of HMG-CoA synthase enzyme which comprises the administration to a subject in need of such treatment a nontoxic therapeutically effective amount of a compound represented by the general structural formula (I) wherein R is hydrogen or $C_{1-3}$ alkyl; the tetrahydro analogs thereof an pharmaceutically acceptable salts thereof. Specifically the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compounds of this invention may also be coadministered with pharmaceutically acceptable nontoxic cationic polymers capable of binding bile acids in a non-reabsorbable form in the gastrointestinal tract. Example of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The intrinsic HMG-CoA synthase inhibition activity of the compounds of this invention is measured by the standard in vitro protocol described below:

The livers from male Charles River CD rats (225–350 g) were homogenized in 0.25M sucrose which was adjusted with phenylmethylsulfonylfluoride (PMSF) and N-p-tosyl-l-lysine chloromethyl ketone (TLCK) so that the final concentration of each was 50 and 25 μg/ml, respectively. The homogenate was centrifuged at 15,000×g for 20 minutes, the supernatant filtered through a fine nylon screen to remove most of the fat layer and recentrifuged at 100,000×g for 1 hour. This supernatant was removed at 1M potassium phosphate, dithiothreitol (DTT) and ethylene glycolbis(β-aminoethyl ether)-N,N,N',N'-tetraacetic acid (EGTA) added to give a final concentration of 0.1M (pH 7.2), 0.5 mM and 0.1 mM, respectively. Solid ammonium sulfate was added to 50% saturation to the protein solution, it was centrifuged at 15,000×g and the supernatent discarded. This precipitated protein could be stored at −70° C. for at least one month with very little loss of activity. The ammonium sulfate precipitate was dissolved in an minimal amount of 0.06M potassium phosphate buffer (pH 7.2) containing 0.5 mM dithiothreitol and 0.1 mM EGTA (referred to as 0.06M phosphate buffer) and dialyzed overnight against 2 liters of the same buffer to remove the ammonium sulfate and to inactivate HMG-CoA lyase [Clinkenbeard, et al., J. Biol. Chem. 250, 3108–3116(1975)].

The dialyzed extract was added to a column of DEAE-52 (Whatman) which had been equilibrated with 0.06M phosphate buffer (10 mg of protein to 1 ml bed volume of the resin). The DEAE-cellulose was eluted with 0.06M phosphate buffer until the optical density at 280 nm was essentially zero. This fraction contained the β-ketoacetyl-CoA thiolase activity. The HMG-CoA synthase was eluted from the column with 0.1M phosphate buffer (pH 7.2) containing 0.5 mM DTT and 0.1 mM EGTA, and was virtually free of all thiolase activity. The protein was precipitated by the addition of ammonium sulfate to give 50% saturation. This solution was stirred for 10 minutes at 4° C. and the precipitate collected by centrifugation at 15,000 rpm for 10 minutes. The supernatant was discarded with the precipitate dissolved in a minimum of 0.06M phosphate buffer, pH 7.2 (about 10 ml) and the enzyme stored at −80° C.

HMG-CoA SYNTHASE INHIBITION ASSAY

Enzyme protein (ca. 24 μg) was added to a solution containing 117 mM Tris-HCl (pH 8.0), 11.7 mM $MgCl_2$, 1.17 mM Ethylenediaminetetraacetic acid (EDTA), 0.58 mM dithiothreitol, and the indicated concentrations of the test compound (added as a 2 μg/ml solution in dimethylsulfoxide). The incubation took place in a volume of 0.085 ml at 30° in a shaking water bath. After 5 minutes, 15 μl of a solution containing acetoacetyl-CoA and 0.1 μCi of 1-[$^{14}$C]-acetyl-CoA was added to give a final concentrations of 0.1 and 0.4 mM, respectively. The incubation was continued for 10 more minutes and the reaction stopped by the addition of 50 μl of the assay mixture to 0.2 ml of 6N HCl in a glass scintillation vial. The vial was heated for 1 hour at 120° after which time 0.2 ml more of 6N HCl was again added to each vial and the heating continued for another hour. Following this, 1.0 ml of 0.9% saline was added to each vial and finally 10 ml of scintillation liquid. Radioactivity was determined in a Packared Tri-Carb liquid scintillation counter.

Percent inhibition is calculated by the formula:

$$1 - \frac{\text{Sample} - \text{Blank}}{\text{Control} - \text{Blank}}$$

$IC_{50}$ values were determined by plotting the log of the concentration of the test compound verses the percentage inhibition and fitting a straight line to the resulting data by using the least squares method.

Representative of the intrinsic HMG-CoA synthase inhibitory activities of the compounds of this invention, tabulated below are the $IC_{50}$ or $IC_{25}$ (the inhibitory concentration which inhibits 50 percent and 25 percent of the HMG-CoA synthase activity respectively).

| Compound | $IC_{50}$ | $IC_{25}$ |
|---|---|---|
| HO, O, O, $CO_2H$ | $1 \times 10^{-7}$ M | — |
| HO, O, O, $CO_2H$ | $3 \times 10^{-7}$ M | — |
| HO, O, O, $CO_2CH_3$ | — | $1.2 \times 10^{-7}$ M |

The compounds of this invention are conveniently prepared as described in *J. Chem. Soc.* (C), 1971 3888–3891 by the fermentation of an identified fungus ACC 1233 and the standard chemical transformations disclosed therein. The compound of the formula (I) wherein R is hydrogen may also be prepared by the cultivation of a member of the class of fungi selected from ATCC 20788, ATCC 20789 or ATCC 20790 followed by a standard isolation.

The morphological characteristics of the microorganisms ATCC 20788, ATCC 20789, and ATCC 20790 are described below:

FUSARIUM SP. MF5045 ATCC 20788

Cultural Characteristics

On Czapek-Dox agar—mycelia is extensive, white and cottony, becoming felted and white with sectors of faint bluish-green tinge or a pale peach tinge as culture ages. Moist areas faint bluish-green in color develop where macroconidia are abundant.

On potato-dextrose agar—mycelia is extensive, white and cottony, becoming felted and pinkish-tan in color as culture ages. When vegatative incoculum is used, moist areas, tan in color, develop where macroconidia are abundant.

On Sabouraud-maltose agar—mycelia is extensive, velvety and white with peach to light purple tinge.

Morphological Characteristics

Microconidia are generally unicellular, oval-ellipsoidal, borne singly and held in a gelatinous mass. 1.8–2.4μ×3.6 to 4.8μ.

Macroconidia are 3 to 5 celled, thin-walled, ends are tapered and slightly curved. 3.6–4.8μ×24–36μ.

Chlamydospores are abundant, terminal and intercalary, globose, generally smooth-walled, usually formed singly but sometimes formed in pairs.

FUSARIUM SP. MF5058 ATCC 20789

Cultural Characteristics

On Czapek-Dox agar—mycelia is extensive, white and cottony, becoming felted and white with sectors of a faint bluish-green tinge or a pale peach tinge as culture ages. Moist areas faint bluish-green in color develop where macroconidia are abundant.

On potato-dextrose agar—mycelia is extensive, white and cottony, becoming felted and pinkish-tan in color as culture ages. When vegatative inoculum is used, moist areas, tan in color develop where macroconidia are abundant.

On Sabouraud-maltose agar—mycelia is extensive, velvety and white with peach to light purple tinge.

Morphological Characteristics

Microconidia are generally unicellular, oval-ellipsoidal, borne singly and held in a gelatinous mass. 1.8–2.4μ×3.6–4.8μ.

Macronconidia are 3 to 5 celled, thin-walled, ends are tapered and slightly curved 3.6–4.8μ×24–36μ.

Chlamydospores are abundant, terminal and intercalary, globose, generally smooth-walled, usually formed singly but sometimes formed in pairs.

FUSARIUM SP. MF 5084 ATCC 20790

Cultural Characteristics

On Czapek-Dox agar-mycelia is expensive, white and cottony, becoming felted and white with sectors of a faint bluish-green tinge or a pale peach tinge as culture ages. Moist areas faint bluish-green in color develop where macroconidia are abundant.

On potato-dextrose agar—mycelia is extensive, white and cottony, becoming felted and pinkish-tan in color as culture ages. When vegetative inoculum is used, moist areas, tan in color, develop where macroconidia are abundant.

On Sabouraud-maltose agar—mycelia is extensive, velvety and deep-pinkish tan in color. Vegetative growth and medium become purplish-red.

Morphological Characteristics

Microconidia are generally unicellular, oval-elliposoidal, borne singly and held in a gelatinous mass 1.8–2.4μ×6–4.8μ.

Macroconidia are 3 to 5 celled, thin-walled, ends are tapered and slightly curved. 3.6–4.8μ×24–36μ.

Chlamydospores are abundant, terminal and intercalary, globose, generally smoothed-walled formed singly but sometime formed in pairs.

The compound of the formula (I) wherein R is hydrogen may be produced by the cultivation of a member of the class of fungi ATCC 20788, ATCC 20789, or ATCC 20790 under the following general conditions.

A preserved source of the culture is used to inoculate an agar slant containing a nutrient medium for growth. After incubation at room temperature for 1 to 5 weeks a portion of this growth is used to inoculate a liquid nutrient medium containing sources of carbon, nitrogen, phosphorus and other elements necessary for life. This medium is incubated at 25° to 30° C., usually 28°. The flask containing the culture and liquid nutrient medium is incubated with or without agitation on a rotary shaker from 0 to 400 RPM, most often at 212 RPM. After 1 to 10 days, when growth is abundant, usually between 2 and 4 days, the culture growth is used to inoculate a flask containing a medium which supports production of the product. Such production media contain carbon sources such as corn, glycerol, corn oil, dextrose, cod oil or peanut meal, nitrogen and sulfur sources such as yeast extract, corn steep liquor, corn, lard water, peanut meal, soy flour, tomato paste and the like as well as organic and inorganic ions such as potassium, phosphorous, clacium, tartrate, iron and magnesium. These production media are inoculated with the culture growth and are incubated at from 20° to 30° most often 25° for 3 to 30 days usually 7–14 days with or without agitation.

The compound of the formula (I) wherein R is hydrogen may be recovered from the fermentation medium by extration with a water miscible solvent, such as $C_{1-3}$ alcohol, especially methanol and water in a ratio from 0.1:1.0 to 1.0 to 0.1, especially 1:1 by volume. The extract is partioned between the aqueous phase and a water miscible organic solvent such as ethyl acetate or methylene chloride. The desired compound is further purified by chromatography on silica gel and then Sephadex LH20 (tradename for dextran derivatives used as gel filtrants in organic solvents, manufactured by Pharmacia Fine Chemicals, Inc.). Finally, the product may be crystallized from aqueous alcohol.

The following examples illustrate the preparation of the compounds and their incorporation into pharmaceutical compositions and as such are not to be construed as limiting the invention set forth in the claims appended hereto.

The composition of media employed in the following examples are listed below. Media are prepared in a 250 ml Erlenmeyer flask. The contents are sterilized with steam at 121° C., 20 pounds pressure for 20 minutes. Media that contain corn are rehydrated and again sterilized with steam at 121° C., 20 pounds pressure for 20 minutes before inoculation.

F867: 10 g/flask corn, 0.1 g/flask $MgSO_4.7H_2O$, 0.01 g/flask $FeSO_4.7H_2O$, 15 ml/flask of (33 g/l yeast extract) after 7 days incubation add 20 ml $H_2O$/flask, incubate without agitation for 14 days F870: 10 g/flask corn, 0.01 g/flask $FeSO_4.7H_2O$, 0.01 g/flask $ZnSO_4.7H_2O$, 15 ml/flask of (33 g/l yeast extract), incubate without agitation for 14 days F872: 10 g/flask corn, 15 ml/flask of (33 g/l yeast extract) incubate without agitation for 7 days then at 220 rpm for 7 days F848: 10 g/flask corn, 15 ml/flask of ($MgSO_4.7H_2O$ 0.1 g/l, Na tartrate 0.1 g/l, $FeSO_4.7H_2O$ 0.01 g/l, $ZnSO_4.7H_2O$ 0.01 g/l) incubate at 220 rpm for 7 days

KF:

Corn Steep 5 g
Tomato Paste 40 g
Oat Flour 10 g
Dextrose 10 g
Distilled water 1000 ml
Trace Element Mix No. 2–10 ml of ($FeSO_4.7H_2O$ 1 g/l, $MnSO_4.4H_2O$ 1 g/l, $CuCl_2.2H_2O$ 25 mg/l, $CaCl_2.2H_2O$ 100 mg/l, $H_3BO_3$ 56 mg/l, $(NH_4)_6Mo_7O_{24}.4H_2O$ 19 mg/l, $ZnSO_4.7H_2O$ 200 mg/l Deionized water 1000 ml) pH 6.8

YME:

Yeast extract 4 g
Malt extract 10 g
Dextrose 4 g
Agar 20 g
pH 7
Distilled water 1000 ml

EXAMPLE 1

Preparation of 12-Hydroxy-13-hydroxymethyl-3,5,7-trimethyltetradeca-2,4-dien-1,14-dioic acid 12,14 lactone (a) Fermentation of ATCC 20790

A culture of ATCC 20790 was inoculated onto YME slant medium. After growth at 25° C., a portion of this slant was used to inoculate a baffled 250 ml Erlenmeyer flask containing KF growth medium (54 ml). The flask was incubated with agitation at 212 rpm on a rotary shaker (2 inch throw) for 3 days at 28° C. Then a portion of the growth (2 ml) was used to inoculate an unbaffled 250 ml Erlenmeyer flask containing Medium F867 (media F870 or F872 may also be employed). After 14 days incubation at 25° C. methanol (20 ml) was added and then let stand overnight. Then water (10 ml) was added to the flask. The desired product was contained in the aqueous methanol extract.

(b) Fermentation of ATCC 20789

(1) A preserved culture source of ATCC 20789 was used to inoculate a baffled 250 ml Erlenmeyer containing KF growth medium (54 ml). The flask was incubated with agitation at 212 rpm on a rotary shaker (2 inch throw) for 3 days at 28° C. Then a portion of the growth (2 ml) was used to inoculate an unbaffled 250 ml Erlenmeyer flask containing medium F870. After 14 days incubation at 25° C., 50 percent aqueous methanol was added. The aqueous methanol extract was employed in the isolation and purification procedure described below.

(c) Fermentation of ATCC 20788

A culture of ATCC 20788 was used to inoculate a baffled 250 ml Erlenmeyer flask containing KF growth medium (54 ml). The flask was incubated with agitation at 212 rpm on a rotary shaker (2 inch throw) for 3 days at 28° C. Then a portion of the growth (2 ml) and remaining medium was used to inoculate an unbaffled 250 ml Erlenmeyer flask containing medium F848. After 7 days incubation at 25° C., the contents of the flask were extracted with methanol (20 ml) in water (10 ml) to obtain the desired product.

(d) Isolation and Purification

The aqueous methanol extracts (700 ml each) from the fermentation medium from two series of fermentations of the microorganism ATCC 20789 according to the general procedure of Example 1(b) were filtered. The first extract was partitioned with methylene chloride (700 ml) and the second extract was partitioned with ethyl acetate (700 ml). In both cases activity was located in the organic phase. The two organic phases were combined and concentrated in vacuo. The residue was dissolved in ethyl acetate/hexane (4:6) (2 ml) and chromatographed on silica gel (200 ml) eluted with a stop gradient of ethyl acetate:hexane (4:6, 6:4, 5:5 and 7:3). The desired product was rechromatographed on LH-20 (20 ml) eluted with methylene chloride:hexane:-methanol (10:10:1) and the desired product eluted from the column with methanol. An analytically pure sample of the title compound was a crystalline compound mp. 76°-77° C.

The $^{13}C$ NMR spectrum was recorded in $CD_3OD$ at ambient room temperature (25 mg/0.4 ml) on a Varian XL 400. Chemical shifts are given in ppm downfield of tetramethylsilane relative to the solvent peak at 49.0 ppm as standard. In agreement with the mass spectral data, 18 carbon atoms are observed with the following chemical shifts: 18.5, 19.8 (2X), 26.4, 27.8, 32.0, 35.0, 37.8, 49.9, 58.0, 60.0, 76.3, 118.7, 130.6, 142.3, 155.7, 170.4, 171.9 ppm.

Mass Spectrum Calc'd for $C_{18}H_{28}O_5+H$: 325.2015. Found 325.2015.

EXAMPLE 2

Preparation of Methyl 12-hydroxy-13-hydroxymethyl-3,5,7-trimethyltetradeca-2,4-dien-1,14-dioic acid 12,14 lactone To a stirred solution of the compound from Example 1(d) (3.2 mg, 0.01 mmol) in anhydrous diethyl ether (0.5 ml) at ambient temperature was added dropwise, diazomethane dissolved in anhydrous diethyl ether until the reaction mixture maintained a bright yellow color. The excess diazomethane was removed by bubbling nitrogen through the reaction mixture. The desired product was purified by preparative thin layer chromatography on silica gel eluted with 1 percent methanol in methylene chloride to afford above titled compound as an oil.

IR spectrum max 3520, 1820, 1705 $cm^{-1}$.

Mass Spectrum Calc'd for $C_{19}H_{30}O_5$ 338. Found: 338.

EXAMPLE 3

Preparation of 12-Hydroxy-13-hydroxymethyl-3,5,7-trimethyltetradecan-1,14-dioic acid 12,14 lactone To a solution of the compound from Example 1(d) (32 mg, 0.01 mmol) in glacial acetic acid (0.5 ml) was added platinum oxide (2 mg) and the compound was hydrogenated at ambient temperature under atmospheric pressure. After one hour, the flask was flushed with nitrogen and the reaction mixture filtered. The filtrate was concentrated in vacuo. The residue was purified by preparative thin layer chromatography on silica gel, eluted with 3 percent methanol in methylene chloride to afford the above titled compound as an oil.

IR spectrum max 1820, 1710 $cm^{-1}$.

Mass spectrum Calc'd for $C_{18}H_{30}O_4$ ($M-H_2O$): 310. Found: 310.

EXAMPLE 4

Preparation of Alkali and Alkaline Earth Salts of Compound I wherein R is hydrogen To a solution of the lactone from Example 1 (42 mg) in ethanol (2 ml) is added aqueous NaOH (1 equivalent). After one hour at room temperature, the mixture is taken to dryness in vacuo to yield the sodium salt of Compound I, wherein R is hydrogen.

In like manner, the potassium salt is prepared using one equivalent of potassium hydroxide, and the calcium salt using one equivalent of CaO.

EXAMPLE 5

As a specific embodiment of an oral composition of a compound of this invention, 20 mg of the lactone from Example 1 is formulated with sufficient finely divided lactose to provide a total amount of 580 to 590 mg to fill a size 0 hard gelatin capsule.

EXAMPLE 6

As specific embodiment of a parenteral composition of a compound of this invention, 20 mg of the lactone from Example 1, as the sodium salt, is dissolved in sterile water, buffered to a pH of 7 with 1.0 mM potassium phosphate buffer solution to a concentration of 2.0 percent and is placed in a sterile ampul for parenteral administration.

What is claimed is:

1. A method of inhibiting the activity of HMG-CoA Synthase enzyme which comprises the administration to a subject in need of such treatment a nontoxic therapeutically effective amount of a compound represented by the following general structural formula (I):

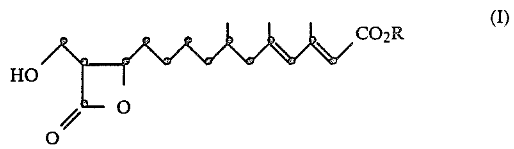

wherein R is hydrogen or $C_{1-3}$ alkyl; a tetrahydro analog therof; or a pharmaceutically acceptable salt thereof.

2. A method of claim 1 for the treatment of arteriosclerosis, hyperlipidemia, or familial hypercholesterolemia.

3. A method of claim 2 in which a daily dosage of from about 20 to 2000 mg of active ingredient is administered.

4. A method of claim 3 in which the active ingredient is administered with a pharmaceutical carrier.

5. A method of claim 4 in which the administration is oral.

6. A method of claim 4 in which the administration is parenteral.

7. A hypocholesterolemic, hypolipidemic pharmaceutical composition comprising a non-toxic therapeutically effective amount of a compound represented by the following general structural formula (I)

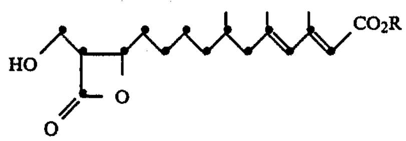

(I)

wherein

R is hydrogen or $C_{1-3}$alkyl;

a tetrahydro analog thereof; or a pharmaceutically acceptable salt thereof in combination with a pharmaceutically acceptable non-toxic cationic polymer capable of binding bile acids in a non-reabsorbable form in the gastrointestinal tract and a pharmaceutically acceptable carrier.

8. A hypocholesterolemic, hypolipdemic pharmaceutical composition of claim 7 wherein the pharmaceutically acceptable non-toxic cationic polymer is selected from the group consisting of cholestyramine, colestipol and poly[methyl-(3-trimethylaminopropyl) imino-trimethylene dihalide].

* * * * *